Figure 1:
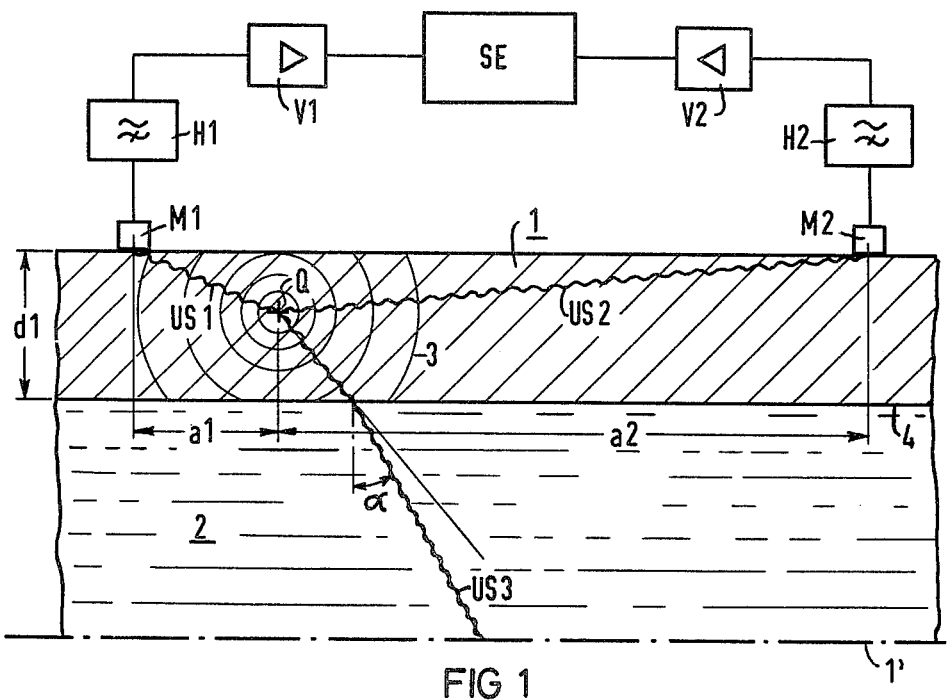

United States Patent [19]
Votava et al.

[11] 4,428,236
[45] Jan. 31, 1984

[54] METHOD OF ACOUSTIC EMISSION TESTING OF STEEL VESSELS OR PIPELINES, ESPECIALLY FOR NUCLEAR REACTOR INSTALLATIONS

[75] Inventors: Erwin Votava, Pforzheim; Günter Stipsits, Neunkirchen; Richard Sommer, Bamberg, all of Fed. Rep. of Germany

[73] Assignee: Kraftwerk Union Aktiengesellschaft, Mülheim, Fed. Rep. of Germany

[21] Appl. No.: 305,512

[22] Filed: Sep. 25, 1981

[30] Foreign Application Priority Data

Sep. 30, 1980 [DE] Fed. Rep. of Germany ....... 3036951

[51] Int. Cl.³ ............................................ G01N 29/04
[52] U.S. Cl. ...................................... 73/587; 376/252
[58] Field of Search .................... 73/587; 376/249, 252

[56] References Cited

U.S. PATENT DOCUMENTS 4,033,179 7/1977 Romrell ................................ 73/587
4,088,907 5/1978 Jones et al.

OTHER PUBLICATIONS

J. Eisenblätter and P. Jax–"Defect Position–Finding and Leak–Testing of Large Vessels and Pipelines with the Air of Acoustic Emission Analysis", (VGB Power Plant Engineering 56, Jul. 1976, Book 7, p. 456).

Primary Examiner—James J. Gill
Attorney, Agent, or Firm—Herbert L. Lerner; Laurence A. Greenberg

[57] ABSTRACT

Method of acoustic-emission testing of a steel component such as a vessel of pipeline especially of primary circulatory loops of nuclear reactor installations wherein the component, on one hand is subjected to a pressure medium, such as water, and, on the other hand, to ultrasonic pulses emitted during deformation development resulting from growth of cracks therein or from leaks and transmitted through the component, which includes detecting and amplifying the ultrasonic pulses with equipment, respectively, formed of test probes, which are disposed so as to determine respective sources of acoustic emission due to differences in transmission time of the ultrasonic pulses through the component, and of electronic amplifiers operatively associated with the test probes, and then feeding a resultant amplified defect signal from the equipment to a display, the equipment being tuned to reception of a frequency band of acoustic-emission spectrum which is above a limiting frequency $f_G$ defined by the relationship:

$$5.9 \leq \frac{f_G \cdot d}{\text{MHz} \cdot \text{mm}} \leq 6.0,$$

wherein d is the wall thickness of the component being tested.

8 Claims, 2 Drawing Figures

$$5{,}9 \leq \frac{f_G \cdot d}{\text{MHz} \cdot \text{mm}} \leq 6{,}0$$

METHOD OF ACOUSTIC EMISSION TESTING OF STEEL VESSELS OR PIPELINES, ESPECIALLY FOR NUCLEAR REACTOR INSTALLATIONS

The invention relates to a method of acoustic emission testing (AET) of steel vessels or pipelines and, more particularly, for testing components of the primary circulatory loop of nuclear reactor installations, wherein the component, on the one hand, is subjected to a pressure medium, such as water, especially, and, on the other hand, ultrasonic pulses emitted during deformation development resulting from growth of cracks or from leaks and transmitted through the component are detected by test probes, especially piezoelectric transducers, which are so disposed that, due to differences in transmission time, respective sources of acoustic emission are determinable, defect signals detected by the test probes being electronically amplified and then fed to display devices.

Such a method is known from the paper "Defect Position-Finding and Leak-Testing of Large Vessels and Pipelines with the Aid of Acoustic Emission Analysis" by J. Eisenblätter and P. Jax (VGB Power Plant Engineering 56, July 1976, Book 7, pages 452 to 456). Acoustic emission testing, also referred to as acoustic emission analysis, is accordingly based upon the phenomenon that, during deformation development or growth of cracks in a material, short acoustic pulses are generated having a frequency range extending far into the ultrasonic range. With sensitive piezoelectric test probes as sound detectors, electromagnetically operating sound detectors being basically also possible, the emitted sound pulses, especially ultrasonic pulses, can be detected. If several test probes i.e. at least three, distributed over the components to be tested, are used, a defect location can be detected with the aid of the so-called triangulation method similar to the localization of the center of an earthquake in seismology. In accordance with the electronic measurement of the difference in transmission time between the individual test probes, the location of the defect is able to be calculated or determined as the source of the sound. In pipelines, a linear orientation or position-finding of the defect by measuring the transmission-time difference between two test probes is generally sufficient.

The advantageous construction of an individual test probe and an appertaining electronic circuit with amplifiers after-connected to the test probes and a cathode ray tube may be learned, for example, from U.S. Pat. No. 4,088,907.

Heretofore, it has been the testing practice to employ the same probes for acoustic-emission testing tuned to a given frequency band, mostly resonant probes between 100 kHz to 300 kHz, both for thick as well as thin-walled vessels, in water-pressure tests. It was found that the water, the required pressure medium in a water-pressure test, has a great influence upon the propagation or spreading of the defect or fault signal, especially the more thin-walled the vessel and a corresponding pipeline, respectively, which is to be tested, is. No clear details as to the location of the defect or fault can then be obtained from the received defect or fault signals because no definite wave propagation speed can be specified as a result of a long ascending flank.

It is accordingly an object of the invention to provide a method of acoustic emission testing of the foregoing general type with which clear and definite fault or defect signals are capable of being derived both for thick as well as thin-walled vessels and pipelines in the presence of acoustic emission sources.

With the foregoing and other objects in view, there is provided, in accordance with the invention, a method of acoustic-emission testing of a steel component such as a vessel or pipeline especially of primary circulatory loops of nuclear reactor installations wherein the component, on one hand, is subjected to a pressure medium, such as water, and, on the other hand, to ultrasonic pulses emitted during deformation development resulting from growth of cracks therein or from leaks and transmitted through the component, which comprises detecting and amplifying the ultrasonic pulses with equipment, respectively, formed of test probes, which are disposed so as to determine respective sources of acoustic emission due to differences in transmission time of the ultrasonic pulses through the component and of electronic amplifiers operatively associated with the test probes, and then feeding a resultant amplified defect signal from the equipment to a display, the equipment being tuned to reception of a frequency band of acoustic-emission spectrum which is above a limiting frequency $f_G$ defined by the relationship:

$$5.9 \leq \frac{f_G \cdot d}{\text{MHz} \cdot \text{mm}} \leq 6.0,$$

wherein d is the wall thickness of the component being tested.

In accordance with another feature of the invention, the test probes are tuned to the frequency band above the limit frequency $f_G$.

In accordance with a further feature of the invention, the amplifiers are tuned to the frequency band above the limit frequency $f_G$.

In accordance with an additional feature of the invention, the test probes and the amplifiers are tuned to the frequency band above the limit frequency $f_G$.

In accordance with an added feature of the invention, the equipment is tuned to a reception restricted for frequency bands below the limit frequency $f_G$.

In accordance with yet another feature of the invention, the equipment is non-resonant for frequency bands below the limit frequency $f_G$.

In other words, there exists for steel a limiting frequency $f_G$, which is dependent on or a function of wall thickness, above which radiation into a liquid medium, such as water, for example, diminishes, the formula recited hereinbefore being able to be written in the manner also customary for plate-wave diagrams, as follows:

$$5.9 \leq f_G \times d \leq 6.0 [mm \cdot MHz].$$

The physical explanation for the foregoing mathematical relationship and the thereby defined wall thickness-dependent limiting or cut-off frequency $f_G$ is primarily in that frequency bands lying below the limiting frequency are radiated from the acoustic emission source into the liquid pressure medium, such as water especially, whereas frequency bands above the limiting frequency make their way as plate waves directly through the material of the component to be tested or do so after one or more interface reflections to the test probes. In the application of the stated dimensioning rule, the test probes therefore make use of only the plate waves traveling in the pipe or tube or in the component.

This results in a sharp ascending flank of the measuring signal with which, accordingly, a definite wave propagation speed is to be associated. A location or orientation accuracy results therefrom, as can be attained in itself in the empty tube or pipe or in an empty component.

In contrast therewith, a blending of the plate waves with the so-called water waves (ultrasonic pulses propagated in the water) results in a velocity depending upon the distance between the AET-signal and the probe when the threshold level is exceeded and thus results in such great location or orientation inaccuracies that the application of acoustic emission testing to thin-walled vessels and pipelines is impossible.

In accordance with yet another feature of the invention, the test probes are broad-band and cooperate with post-staged preamplifiers having a high-pass filtered limiting frequency $f_G$.

In accordance with a concomitant feature of the invention, the test probes proper are resonant above the limiting frequency $f_G$ but limited or non-resonant below the limiting frequency $f_G$.

Other features which are considered as characteristic for the invention are set forth in the appended claims.

Although the invention is illustrated and described herein as embodied in method of acoustic emission tesing of steel vessels or pipelines, especially for nuclear reactor installations, it is nevertheless not intended to be limited to the details shown, since various modifications and structural changes may be made therein without departing from the spirit of the invention and within the scope and range of equivalents of the claims.

Figure 2:
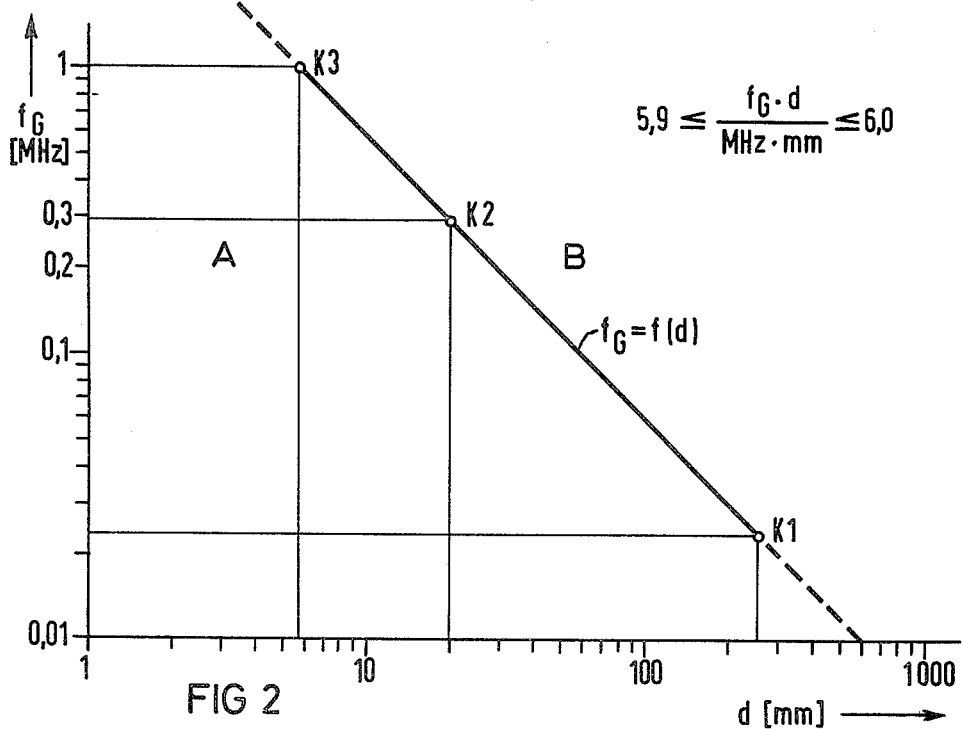

The construction and method of operation of the invention, however, together with additional objects and advantages thereof will be best understood from the following desciption of specific embodiments when read in connection with the accompanying drawings, in which:

FIG. 1 is a fragmentary diagrammatic sectional view, partly schematic, (not according to scale) of a pipe wall with two test probes set up on the exterior of the pipe wall at varying distances from an acoustic emission source; and FIG. 2 is a plot diagram wherein, on a log-log scale, the frequency $f_G$ in MHz is plotted on the ordinate axis, and the wall thickness d in mm is plotted on the abscissa axis, the limiting or cutoff frequency $f_G=f(d)$ having a rectilinear characteristic for the frequency range between 10 kHz and 1 MHz, which is especially of practical interest.

Referring now to the drawing and first, particularly, to FIG. 1 thereof, there is shown a pipeline 1 with a pipeline axis 1' having an exaggeratedly great wall thickness d1., the pipeline accommodating a pressure medium 2, in this case, water under test pressure. Due to the internal pressure load, a tensile stress is exerted upon the pipeline 1, the tensile stress, for example at the point Q, creating a deformation process or crack in the material interior which, as indicated by the wave circles 3, causes the emission of an acoustic signal. Ultrasonic waves US originating from the emission source Q impinge on both test probes M1 and M2. The test probe M1 is set up and secured on the outside of the pipe circumference at an axial spacing a1, and the test probe M2 at an axial spacing a2 from the acoustic source Q. Linearly locating the source Q is effected by means of the test probes M1 and M2, respectively post-staged high passes or high-pass filters H1 and H2, preamplifiers V1 and V2, and an electronic locator and valuating device SE post-staged or after-connected and common to above electronic elements. To understand the invention, the aforementioned representation is believed to be sufficient; in the interest of simplicity, a detail circuit diagram has been omitted; however, it may be obtained, for example, from U.S. Pat. No. 4,088,907, specifically FIG. 9 thereof. Preferably, piezoelectric transducers are used as the test probes M1 and M2. The ultrasonic waves traveling towards the test probe M1 are identified by the reference character US1, those traveling towards the test probe M2 by US2, and those ultrasonic waves radiating into the liquid pressure medium 2 by US3. On the transition from the pipe 1 into the medium 2 (boundary surface 4), the beam US3 is refracted from the perpendicular; the angle of refraction $\alpha$, which is not to scale, is plotted only for purposes of illustration. For the most exact coverage possible, according to the invention, of the transition time differential $\Delta t$ effective between US1 and US2, the testing or measuring is limited to the material or plate waves US 1 and US 2, so that any interference effects produced by the radiated water waves US 3 are eliminated.

FIG. 2 shows the "permitted" frequency wall thickness area B, which is separated from the area A by the characteristic curve $f_G=f(d)$, and within which, in an acoustic emission test of steel structural elements, and extensive radiation of acoustic emission waves into the water occurs. In FIG. 2, the equation or relationship of values in MHz and mm $$5.9 \leq \frac{f_G \cdot d}{\text{MHz} \cdot \text{mm}} \leq 6.0$$

is plotted. Naturally, this equation is an approximation equation which is accurate for practical work; adjacent the cutoff or limiting characteristic $f_G$, smooth transitions or junctions exist. What is essential, however, is that a feasibility exists now for selecting operating ranges for the test probes and associated electronic amplifiers, over which reliable test results can be obtained. Thus, note characteristic point K1, for a reactor pressure vessel having a wall thickness of 250 mm, this results in a bottom limiting or cutoff frequency $f_G$ of about 0.023 MHz i.e. acoustic emission signals having a frequency lower than that are preferably radiated into the water and are not available any more for the testing process; this requires then the use of test probes and/or associated band-pass filtered electronic amplifiers, which are tuned to receiving the acoustic emission spectral frequency band exceeding this upper cutoff frequency but which are not tunable to or are resonant for frequency bands lower than $f_G$. Another case is exemplified by the characteristic point K2: This involves a pipeline having a wall thickness of 20 mm, where the associated cutoff frequency $f_G$ is about 0.295 MHz. To subject a pipeline with such a wall thickness to an acoustic emission test, the hereinaforestated applies to the tuning of the test probes and/or associated electronic amplifiers accordingly. The characteristic point K3 lies exactly at a point of coordination with the cutoff frequency of 1 MHz and the associated wall thickness of about 5.9 mm. The area above the characteristic $f_G$ is shown only by 2 broken lines because of its lesser importance for acoustic emission tests practiced in mechanical engineering, and especially in nuclear reactor engineering, the more so because, with wall thicknesses becoming thinner, this clear border line between the areas A and B disappears due to a mixture of effects e.g. damping effects. Accordingly, the practice of this method calls for the use of broad-band test probes with post-staged preamplifiers or amplifiers having a high-pass filtered cutoff frequency $f_G$, these amplifiers being readily constructed so as to be tunable to the respective frequency bands in question. To intensify or boost this high-pass effect even more so the test probes themselves can be made resonant above the respective cutoff frequency $f_G$ in question, these test probes being restricted or non-resonant below the $f_G$-level.

The diagram according to FIG. 2 is applicable to the current type of structural steel used, specifically ferritic steel.

The method according to the invention is applicable also to vessels and pipes under external water loads e.g. submarines or floating legs of oil pumping rigs or platforms. In this case, the test probes are set up internally and, upon setting the correct frequency level above $f_G$, effect a continuous monitoring of cracks (and leaks), provided the operating noises are kept low.

As aforementioned, the acoustic emission testing (AET) is used also for detecting and locating leaks. In this case, a continuous acoustic emission signal is involved. But even here, the method succeeds in effecting a better quantification of the leakage and in improving the locating process, because any blending or mixing with the water waves is avoided to the greatest possible extent.

There are claimed:

1. Method of acoustic-emission testing of a steel component such as a vessel or pipeline especially of primary circulatory loops of nuclear reactor installations wherein the component, on one hand is subjected to a pressure medium, such as water, and, on the other hand, to ultrasonic pulses emitted during deformation development resulting from growth of cracks therein or from leaks and transmitted through the component, which comprises detecting and amplifying the ultrasonic pulses with equipment, respectively, formed of test probes, which are disposed so as to determine respective sources of acoustic emission due to differences in transmission time of the ultrasonic pulses through the component, and of electronic amplifiers operatively associated with the test probes, and then feeding a resultant amplified defect signal from the equipment to a display, the equipment being tuned to reception of a frequency band of acoustic-emission spectrum which is above a limiting frequency $f_G$ defined by the relationship:

$$5.9 \leq \frac{f_G \cdot d}{\text{MHz} \cdot \text{mm}} \leq 6.0,$$

wherein d is the wall thickness of the component being tested.

2. Method according to claim 1 wherein the test probes are tuned to the frequency band above the limit frequency $f_G$.

3. Method according to claim 1 wherein the amplifiers are tuned to the frequency band above the limit frequency $f_G$.

4. Method according to claim 1 wherein the test probes and the amplifiers are tuned to the frequency band above the limit frequency $f_G$.

5. Method according to claim 1 wherein the equipment is tuned to a reception restricted for frequency bands below the limit frequency $f_G$.

6. Method according to claim 1 wherein the equipment is non-resonant for frequency bands below the limit frequency $f_G$.

7. Method according to claim 1 wherein the test probes are broad-band and cooperate with post-staged preamplifiers having a high-pass filtered limiting frequency $f_G$.

8. Method according to claim 1 wherein the test probes proper are resonant above the limiting frequency $f_G$ but limited or non-resonant below the limiting frequency $f_G$.

* * * * *